United States Patent [19]

Hasegawa et al.

[11] 4,101,435

[45] Jul. 18, 1978

[54] MAGNETIC IRON OXIDE-DEXTRAN COMPLEX AND PROCESS FOR ITS PRODUCTION

[75] Inventors: Masakatsu Hasegawa, Nagoya; Syusaburo Hokkoku, Kani, both of Japan

[73] Assignee: Meito Sangyo Kabushiki Kaisha, Nagoya, Japan

[21] Appl. No.: 695,925

[22] Filed: Jun. 14, 1976

[30] Foreign Application Priority Data

Jun. 19, 1975 [JP] Japan .................. 50-73754

[51] Int. Cl.² .............. H01F 1/00; A61K 29/02; A61K 33/26
[52] U.S. Cl. ................. 252/62.53; 252/62.54; 424/174; 428/900; 536/113
[58] Field of Search .............. 252/62.53, 62.52, 62.54; 536/113; 428/900; 424/174

[56] References Cited

U.S. PATENT DOCUMENTS

| | | | |
|---|---|---|---|
| 2,360,327 | 10/1944 | Bailey et al. | 252/8.5 C |
| 2,856,366 | 10/1958 | Novak et al. | 252/313 R X |
| 2,971,916 | 2/1961 | Schleicker et al. | 252/62.53 |
| 2,978,414 | 4/1961 | Harz et al. | 252/62.53 X |
| 3,041,289 | 6/1962 | Katchen et al. | 252/62.53 X |
| 3,100,202 | 8/1963 | Muller et al. | 536/113 |
| 3,776,987 | 12/1973 | Grimes et al. | 264/5 |

OTHER PUBLICATIONS

Synowiedzki, Chemical Abstracts, vol. 57, Abstract 9966h (1962).
Hideo, Chemical Abstracts, vol. 56, Abstract 4878g (1962).

*Primary Examiner*—F.C. Edmundson
*Attorney, Agent, or Firm*—Sherman & Shalloway

[57] ABSTRACT

A magnetic iron oxide-dextran complex. This novel compound can be produced by reacting an aqueous sol of magnetic iron oxide with dextran having an intrinsic viscosity of about 0.02 to about 0.5 at an elevated temperature in an aqueous medium, and is useful not only in pharmaceutical and medical fields as a hematinic medium, a radiopaque medium, a blood measuring agent, or a carrier for a medicinal substance, but also in wide range of other technological fields where its magnetic property can be utilized.

14 Claims, 8 Drawing Figures

MAGNETIC IRON OXIDE-DEXTRAN COMPLEX AND PROCESS FOR ITS PRODUCTION

This invention relates to a novel compound, especially a magnetic iron oxide-dextran complex. More specifically, the invention relates to a useful magnetic iron oxide-dextran complex which finds utility not only in pharmaceutical and medical fields as a hematinic medium (iron-deficiency anemia), a radiopaque medium, a blood stream measuring agent, or a carrier for a medicinal substance used at the time of the concentrated administration of the medicinal substance to an affected part of the body utilizing a magnetic field, but also in a wide range of other technological fields where its magnetic property can be utilized, for example, as a mechanical sealing material, a magnetic clutch, a magnetic paint or ink, or a medium in fluid dynamic research. In particular, the invention relates to a magnetic iron oxide-dextran complex which can be formed into a stable aqueous sol by being dissolved in water, is low in toxicity and easy to produce, and which is expected to be utilized in a still wider range of applications including the fields cited above; and to a process for its production.

Magnetic fluids in a broad sense including magnetic iron oxide sols have been known, and are described, for example, in Sov. Phys. — Usp., Vol. 17, No. 2, Sep.-Oct., 1974, pp. 153–169.

There have been roughly two types of processes for producing magnetic iron oxide sols. One type comprises milling a magnetite powder in a liquid medium such as water or kerosene in the presence of a surface active agent such as oleic acid salts, polyisobutyric acid or dodecylamine using a ball mill until it becomes sol-like fine particles, as disclosed, for example, in U.S. Pat. No. 3,700,595. The other type involves a chemical means instead of a mechnical means to produce a magnetic iron oxide sol. According to this type, an aqueous solution of a mixture of a ferrous salt and a ferric salt in which the anion is monovalent and the molar ratio of the ferric ion to the ferrous ion is about 3:1 to 1:1 is gradually added to an aqueous slurry containing an excessive amount of a strongly basic anion exchange resin of the -OH type in such proportions and concentrations that the pH of the mixture is maintained at about 7.5 to about 9.5, and the resulting sol is stabilized by reducing its pH rapidly to 1–3, as disclosed, for example, in U.S. Pat. No. 3,480,555. Preferably, the stabilization is facilitated by adding a surfactant.

Attempts have been made to utilize the magnetic iron oxide sols so produced as mechanical sealing materials, magnetic clutches, or magnetic inks, etc. Since, however, these sols suffer from unsatisfactory long-term storage stability and are unstable to electrolytes such as alkalies or salts, they tend to gel or separate into two phases.

On the other hand, investigations relating to magnetism and the living body have become active in recent years. But no attempt has been made so far to utilize the conventional magnetic sols for therapeutic purposes mainly because these sols are likely to develop serious side effects such as hemolysis in intravital administration.

We have made investigations in order to remove the defects of the conventional magnetic iron oxide sols with regard to their stability and restrictions on the range of their utility. These investigations led to the discovery that a novel magnetic iron oxide-dextran complex heretofore unknown can be provided, and that when this novel complex is dried to form a powder and then re-dissolved in water, it easily forms an aqueous sol. We have also found that the aqueous sol of this novel complex has outstanding stability and withstands storage for long periods of time without gellation or phase separation; and that it does not gel or separate into two phases even in the presence of electrolytes such as alkalies or salts. It has also been found that the novel complex is very low in toxicity as represented by its $LD_{50}$ (mouse, intravenation) of 2000 to 6000 mg/kg calculated as iron, in contrast to the $LD_{50}$ of the conventional magnetic iron oxide sols which is 300 to 600 mg/kg. We have also discovered that this novel complex can be easily produced by a simple and advantageous operation of reacting a conventional aqueous sol of magnetic iron oxide with dextran at elevated temperatures in an aqueous medium.

It is an object of this invention therefore to provide a novel magnetic iron oxide-dextran complex.

Another object of this invention is to provide a process for producing the novel complex.

Many other objects and advantages of this invention will become apparent from the following description.

The magnetic iron oxide-dextran complex of this invention can be easily produced by reacting an aqueous sol of magnetic iron oxide with dextran, preferably dextran having an intrinsic viscosity $[\eta]$ of about 0.02 to about 0.5 in an aqueous medium at an elevated temperature. Preferably, the molar ratio of the aqueous sol of magnetic iron oxide to the dextran is 1 : about 1–5 in terms of the molar ratio of the iron atom in the oxide to the anhydrous glucose unit (A.G.U. for short) of the dextran.

The use of magnetic iron oxide sols prepared by a chemical means gives favorable results in the present invention. Such a sol can be prepared, for example, by mixing an aqueous solution containing a ferric salt and a ferrous salt in suitable proportions with an aqueous solution of an alkaline substance such as sodium hydroxide, potassium hydroxide, lithium hydroxide or ammonium hydroxide, separating the solid from the resulting product, redispersing the separated solid in water, and peptizing the solid by adjusting the pH of the dispersion to the acidic side, for example, about 1–3 with an acid such as hydrochloric acid, and if desired, purifying it by such means as dialysis against running water or ultra-filtration.

Such a sol can also be produced by mixing an aqueous slurry of a strongly basic ion exchange resin with an aqueous solution with a monovalent anion containing a ferric salt and a ferrous salt in suitable proportions so that the pH of the mixture will be maintained preferably at about 7.5 to 9.5, and adjusting the pH of the resulting mixture (containing the sol product) preferably to about 1–3, and if desired, purifying the product in the same manner as described above.

In the formation of the starting magnetic iron oxide sol by the chemical means described above, the magnetic property of the resulting sol can be controlled by adjusting the molar ratio of the ferric ion to the ferrous ion. Preferably, the molar ratio of the ferric ion to the ferrous ion is adjusted to 1:1 to 3:1. When it is desired to obtain a starting magnetic iron oxide sol having a higher saturation magnetic flux density, it is preferred to adjust the above mol ratio to about 2:1.

The starting magnetic iron oxide sol obtained in the above-mentioned manner can be used directly as a material for producing the novel complex of this invention, but if desired, it may be used after concentration. The iron oxide so obtained is believed to be a magnetic iron oxide having a spinel structure which is possessed, for example, by magnetite ($Fe_3O_4$) and maghemite ($\gamma$-$Fe_2O_3$).

The magnetic iron oxide-dextran complex of this invention can be easily formed by heating the magnetic iron oxide sol and dextran in an aqueous medium. Preferably, the starting magnetic iron oxide sol is used after adjusting its pH to about 2.5–4.5. The starting dextran has an intrinsic viscosity [$\eta$] of preferably about 0.02 to about 0.5, more preferably about 0.4 to about 0.1. Glucan mainly having an $\alpha$-1,6-linkage formed by reacting a leuconostoc mesenteroide with sucrose is a preferred example of the dextran used in this invention. More preferably, the dextran may be modified prior to use by heating it in a manner known per se in an aqueous medium in the presence of an appropriate base such as sodium hydroxide, potassium hydroxide or calcium hydroxide.

The intrinsic viscosity [$\eta$] of the dextran is measured in an aqueous solution of 25° C, and defined as follows:

$$[\eta] = \lim_{c \to o} \eta_{sp}/C$$

wherein
$\eta_{sp} = (\eta - \eta_o)/\eta_o = \eta/\eta_o - 1$
$\eta$ = the viscosity of the solution,
$\eta_o$ = the viscosity of the solvent,
$C$ = the concentration in grams/100 ml.

According to one preferred embodiment of producing the magnetic iron oxide-dextran complex of this invention, an aqueous solution of dextran in a concentration of about 10 to about 25 weight/volume percent (the percent of the weight of the dextran based on the volume of water) is mixed with the magnetic iron oxide aqueous sol such that the molar ratio of the iron atom of the oxide to the A.G.U. of dextran is 1 : about 1–5, more preferably 1 : about 1.5–3. The reaction proceeds smoothly by merely heating the reaction mixture. The reaction is performed preferably at a temperature of about 50°–120° C, more preferably about 70°–110° C, but usually it is carried out under reflux. The reaction can be completed, for example, in about 30 to 60 minutes under reflux.

The magnetic iron oxide-dextran complex so formed is separated by adding a water-miscible poor solvent, for example, lower alcohols such as methanol, ethanol or isopropanol, and ketones such as acetone or methyl ethyl ketone to precipitate the complex, and collecting the precipitate. For example, the complex can be precipitated by adding the water-miscible organic solvent to the above reaction mixture in an amount almost equal to the volume of the latter to about one-third of the volume of the latter. The separated precipitate, if desired, is redissolved in water, and if desired, filtered to remove the insoluble matter, and then purified by such means as dialysis against running water. Furthermore, the pH is adjusted, if desired, to about 5–7, and by such a means as concentration at reduced pressure, a magnetic iron oxide-dextran complex aqueous sol of the desired concentration can be prepared. If further desired, the aqueous sol may be made into a solid powdery magnetic iron oxide-dextran complex by drying it by any desired means which does not impart excessive heat thereto such as spray drying or lyophilization; or by adding the alcohol or ketone illustrated above to the aqueous sol to re-precipitate it, collecting the precipitate and drying it at reduced pressure.

The novel complex of this invention can be clearly distinguished from the known iron oxide-dextran complex in that the novel complex of the present invention has magnetic property, and that the dextran is bonded to the starting magnetic iron oxide.

The novel complex of this invention in the solid form prepared in the above-described manner is soluble in water, and a solution of this complex in water forms a stable aqueous sol. Furthermore, the novel complex of this invention does not gel or separate into two phases even upon the addition of electrolytes, but remains as a stable aqueous sol. Such superior stability is the property by which it can be distinguished clearly from the conventional magnetic iron oxide sol. For example, when 2.5 g of the complex of this invention in a solid form is dissolved in 10 cc of water, and the solution is allowed to stand for 24 hours in a constant-temperature tank at 70° C, the state of the aqueous sol at the time of dissolving is maintained, and no gellation nor phase separation occurs. Furthermore, when a 2N aqueous solution of sodium hydroxide is added to the aqueous sol in an amount equal to the volume of the latter, and the mixture is maintained at 20° C. for 1 hour, no gellation nor phase separation is observed. Similarly, no gellation nor phase separation is observed even when a 20% aqueous solution of sodium chloride is added to the aqueous sol in an amount equal to the volume of the latter and the mixture is maintained at 50° C for 24 hours. The above test conditions, therefore, can be used to distinguish the novel complex of this invention from the known magnetic iron oxide sols. Furthermore, the results of the above tests can be utilized to distinguish the novel complex of this invention from a mere mixture of magnetic iron oxide sol and dextran. The mere mixture does not re-dissolve in water under the test conditions, nor does it return to a sol of magnetic iron oxide. It is readily gelled or separated into two phases as a result of adding a 2N aqueous solution of sodium hydroxide or a 20% aqueous solution of sodium chloride.

The magnetic iron oxide-dextran complex of this invention has magnetic property and a saturation magnetic flux density of more than 0, usually not more than about 90 emu/g. According to a preferred embodiment, there is provided a complex having a saturation magnetic flux density of about 5 to about 80 emu/g. In the complex of this invention, about 0.1 to about 1 mole of dextran (calculated as A.G.U. of the dextran) is present per mole of iron (calculated as an atom).

The amounts of the dextran and iron in the complex of this invention are determined by the following methods. Determination of the dextran and iron (Fe):

(1) Preparation of Sample Solution [I]

About 2 g of the magnetic iron oxide-dextran complex in a dry powdery form was precisely weighed, and 15 ml of conc. hydrochloric acid was added to dissolve it completely. Then, distilled water was added to adjust the total amount of the solution to 100 ml.

(2) Dextran Content

It was measured in accordance with the method disclosed in "Analytical Chemistry", Vol. 25, No. 11, pp. 1656–1661 (1953). 10 ml of 0.2% anthrone in 95% sulfuric acid and 4 ml of distilled water were taken in a test tube having a size of 25 × 200 mm, thoroughly mixed, and cooled to 10° to 15° C. Then, 1 ml of a sample solution [II] obtained by diluting the sample solution [I] with distilled water to a dextran content of about 0.1 to 0.2 mg/ml, and they were thoroughly mixed. Then, the mixture was maintained in boiling water for 7 minutes, and immediately then, cooled to room temperature in cold water. The absorbance of the sample solution was measured at a wavelength of 6250 Å in a 10 m/m glass cell using distilled water as a control. As a blank, 1 ml of distilled water was added instead of the sample solution, and the same procedure was taken. A standard dextran solution of a known dextran content was processed similarly.

The dextran content A [mg/ml] of the sample solution [I] is obtained from the following equation.

$$A = (E_a - E_b / E_s - E_b) \times W \times \text{dilution ratio} \quad (1)$$

$E_a$: the absorbance of the sample,
$E_b$: the absorbance of the blank,
$E_s$: the absorbance of the standard solution,
$W$: the dextran content of the standard solution (mg/ml)

(3) Iron (Fe) content

It was measured in accordance with the method disclosed in Nippon Kagaku Zasshi, Vol. 87, No. 7, pp. 681–685. Specifically, 7 ml of a 0.1% o-phenanthroline reagent (dissolved in 2 moles/liter of a $CH_3COOH$—$CH_3COONa$ buffer having a pH of 5.0) and 1 mol of a 10% aqueous solution of hydroxylamine hydrochloride were taken into a test tube (16 × 160 mm). Then, 2 ml of a sample [III] obtained by diluting the sample solution [I] with distilled water to an iron (F) content of 10 to 50 μg/2 ml was added, and they were thoroughly mixed. After a lapse of 30 minutes, the absorbance of the sample was measured at a wavelength of 5100 Å using distilled water as a control in a glass cell (10 mm). As a blank, 2 ml of distilled water was added instead of the sample solution, and the same procedure as above was taken. The same procedure was taken with regard to a standard aqueous solution of Mohr's salt $[FeSO_4\cdot(NH_4)_2 SO_4\cdot 6H_2O]$ having a known iron content.

The iron (Fe) content B [mg/ml] of the sample solution [I] is obtained from the following equation.

$$B = (E_a - E_b / E_s - E_b) \times W \times \text{dilution ratio} \quad (2)$$

$E_a$: the absorbance of the sample,
$E_b$: the absorbance of the blank,
$E_s$: the absorbance of the standard solution,
$W$: the iron (Fe) content [mg/ml] of the standard solution.

(4) Dextran (A.G.U.)/1 atom of iron (Fe) molar ratio

Using A and B given by equations (1) and (2), the molar ratio is calculated from the following equation (3).

$$\text{Dextran (A.G.U.)/1 atom iron (Fe) molar ratio} = A/B \times 55.9/162 \quad (3)$$

The complex of this invention can be distinguished from the conventional iron oxide-dextran complexes having no magnetic property both in X-ray diffraction pattern and infrared absorption specgrum.

Typical examples are shown in FIGS. 1 to 8 of the accompanying drawings.

Other complexes of this invention show similar charts to those shown in FIGS. 1, 3, 5 and 7.

It will be appreciated that the novel complex of this invention can be distinguished from the most analogous conventional non-magnetic iron oxide-dextran complex not only in the possession of magnetic property but also in X-ray diffraction pattern and innfrared absorption spectrum. Furthermore, as is clear from FIGS. 1 and 3, the novel complex of this invention shows in its X-ray diffraction a pattern having a diffraction intensity corresponding to a spinel structure.

The magnetic property of the magnetic iron oxide-dextran dextran complex of the invention is characterized mainly by the magnetic property of the starting magnetic iron oxide sol, and affected by the ratio of bonding between the magnetic iron oxide and dextran, that is, the moles of dextran (calculated as A.G.U.) per mole of magnetic iron oxide (calculated as iron atom). Accordingly, by properly choosing the magnetic property of the magnetic iron oxide sol and the molecular weight, for example, [η], of dextran, complexes having the desired magnetic property can be easily obtained.

The acute toxicity ($LD_{50}$) of the complex of this invention determined by intravenous administration to mouse is 2000 to 6000 mg/kg as iron, whereas that of an aqueous sol of magnetic iron oxide is 300 to 600 mg/kg.

The magnetic iron oxide-dextran complex obtained by the present invention can be used in a wider range of applications than the conventional magnetic iron oxide sols, and is useful, for example, in pharmaceutical and medical fields as a hematinic medium, a radiopaque medium, a blood stream measuring agent, or a carrier for a medicinal substance used at the time of the concentrated administration of the medicinal substance to an affected part of the body utilizing a magnetic field.

The following Examples illustrate the present invention more specifically.

EXAMPLE 1

A mixture of 200 ml of a 1 M aqueous solution of ferric chloride and 100 ml of a 1 M aqueous solution of ferrous chloride was rapidly added with stirring to 840 ml of 1N sodium hydroxide at about 80° C. The resulting precipitate was separated, re-dispersed in 500 ml of water, and peptized by adjusting its pH to about 1.4 using conc. hydrochloric acid. Then, the product was dialyzed against running water for 15 hours to yield an aqueous sol of magnetic iron oxide (having a pH of 3.1 and an iron concentration of 30.9 mg/ml).

On the other hand, 200 g of dextran having an intrinsic viscosity of 0.068 was dissolved in 1000 ml of water, and 20 ml of a 40% aqueous solution of sodium hydroxide was added. The mixture was heated under reflux for 1 hour, and cooled. Methanol was then added, and the dextran precipitated was dissolved in water. The aqueous solution was passed through an ion exchange resin to adjust the dextran concentration to 22%. To 340 ml of the resulting aqueous solution was added 405 ml of the aqueous sol of magnetic iron oxide prepared previously, and the mixture was heated under reflux for 40 minutes. After cooling, 610 ml of methanol was added to precipitate the complex. The precipitate was dissolved in water, and dialyzed against running water for 24 hours. The pH of the solution was adjusted to 6.5 using an aqueous solution of sodium hydroxide. Then, the solution was concentrated at reduced pressure, filtered, and lyophilized to afford 21 g of a powdery complex having 45.5 W/W % of iron. The product had a saturation magnetic flux density of 37 emu/g and an acute toxicity ($LD_{50}$) of 4100 mg/kg calculated as iron.

Figure 1:
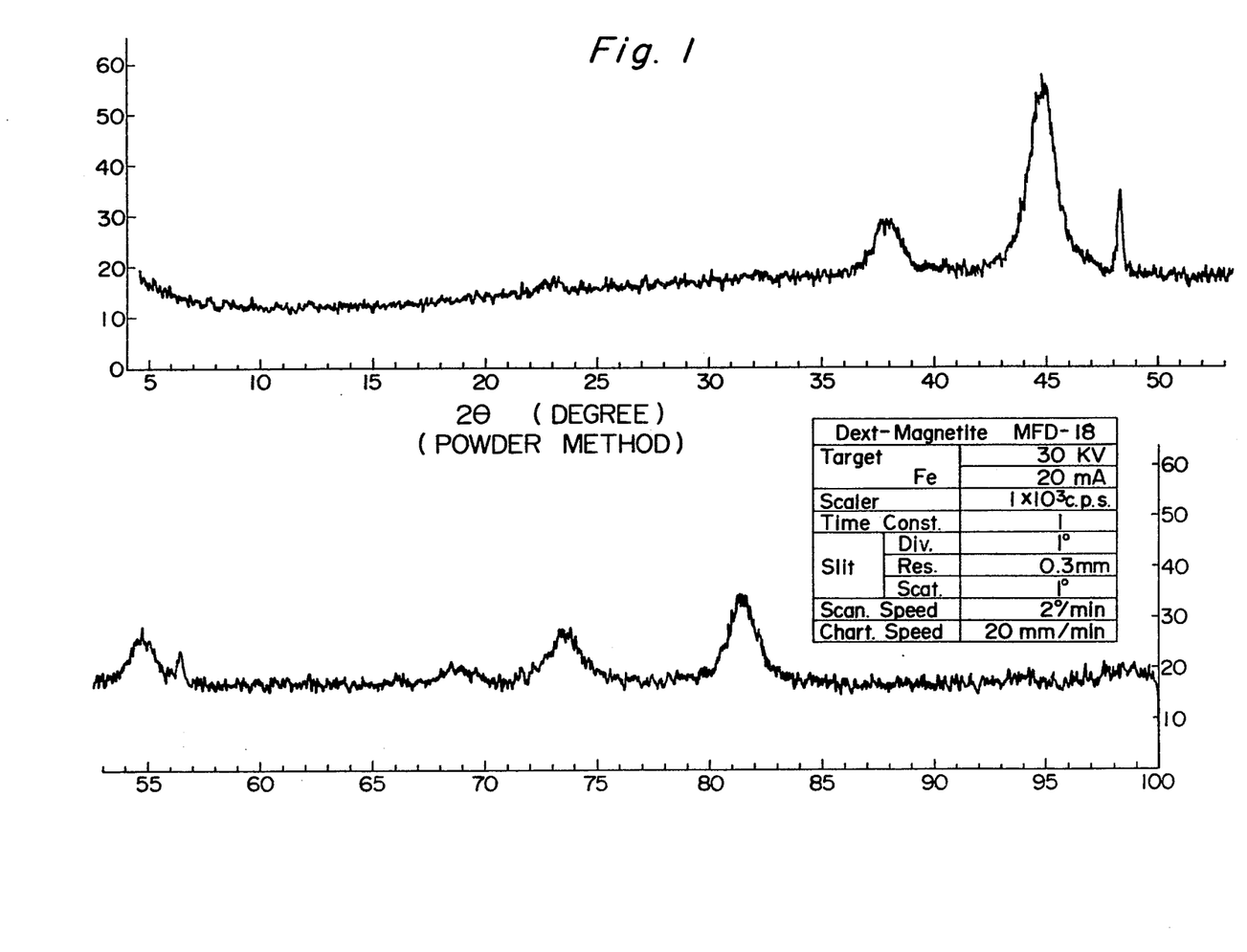
FIG. 1 is an X-ray diffraction chart of the complex obtained in Example 1 of this application.
Figure 2:
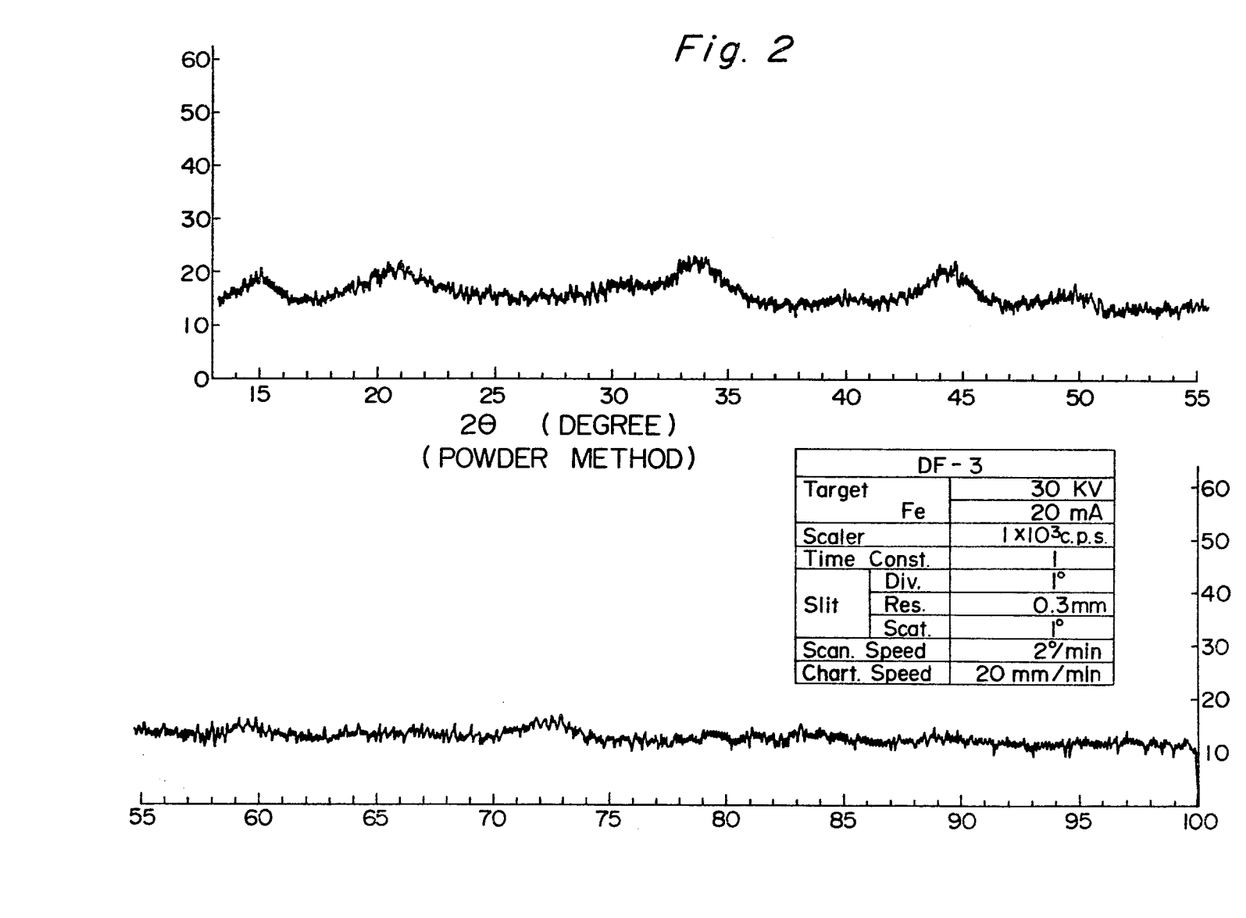
FIG. 2 is an X-ray diffraction chart of the conventional non-magnetic iron oxide-dextran complex obtained by using the same dextran as used in Example 1 of the application.
Figure 5:
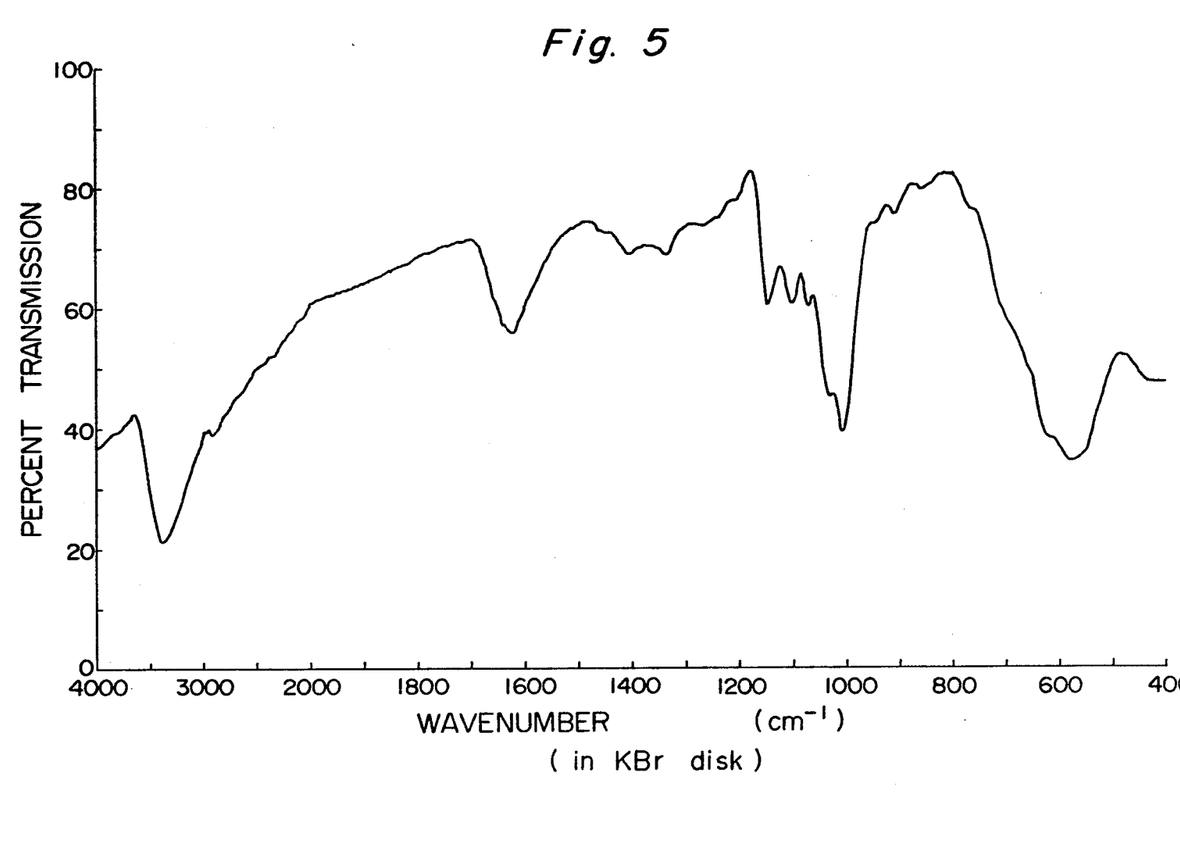
FIG. 5 is an infrared absorption spectrum chart of the complex obtained in Example 1 of the application.
Figure 6:
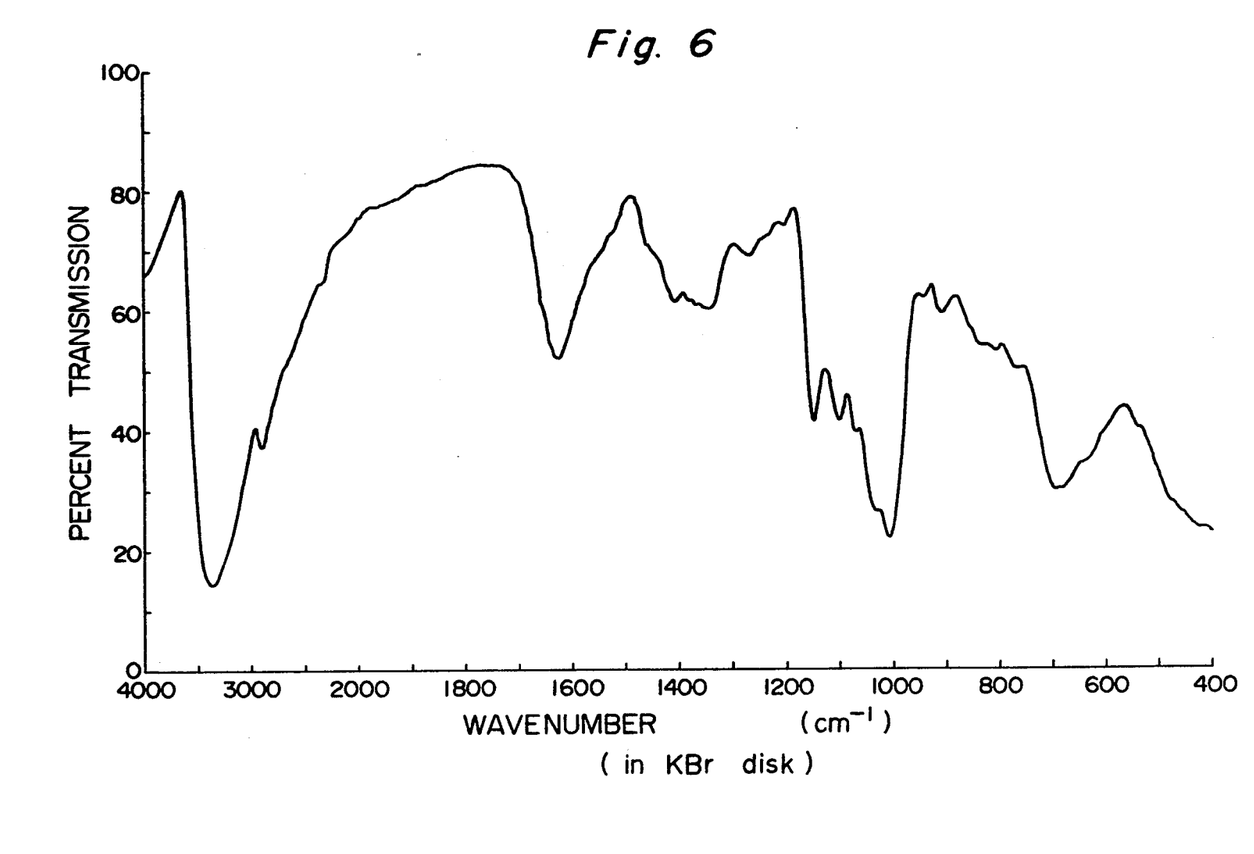
FIG. 6 is an infrared absorption spectrum chart of a conventional non-magnetic iron oxide-dextran complex obtained by using the same dextran as used in Example 1.

The X-ray diffraction chart of the complex obtained is shown in FIG. 1 and its infrared absorption spectrum, in FIG. 5.

EXAMPLE 2

200 g of dextran having an intrinsic viscosity of 0.173 was dissolved in 1500 ml of water, and 10 ml of a 40% aqueous solution of sodium hydroxide was added. The mixture was heated under reflux for 1.5 hours, and cooled. Then, methanol was added. The dextran precipitated was dissolved in water, dialyzed against running water for 24 hours, and concentrated at reduced pressure to adjust the dextran concentration to 15%. To 670 ml of the resulting aqueous solution was added 405 ml of the aqueous sol of magnetic iron oxide prepared in Example 1, and the mixture was heated under reflux for 1 hour. After cooling, 830 ml of methanol was added to precipitate the resulting complex. The precipitate was dissolved in water. The re-precipitation operation using water-methanol was repeated, and the resulting precipitate was dried at reduced pressure to yield 29 g of a powdery complex. The saturation magnetic flux density of the product (having an iron content of 33.6 W/W %) was 27 emu/g, and its acute toxicity ($LD_{50}$) was 3200 mg/kg as iron.

EXAMPLE 3

An aqueous solution of dextran having an intrinsic viscosity of 0.068 was passed through an ion exchange resin to adjust the dextran concentration to 23%. To 330 ml of the aqueous solution, 405 ml of the aqueous sol of magnetic iron oxide prepared in Example 1 was added, and the mixture was heated under reflux. It was cooled, and filtered. Then 590 ml of methanol was added to precipitate the complex. The precipitate was dissolved in water, and the pH of the aqueous solution was adjusted to 5.5. Subsequent lyophilization gave 18 g of a powdery complex. This product had an iron content of 45.5 W/W %, a saturation magnetic flux density of 36 emu/g, and an acute toxicity ($LD_{50}$) of 2300 mg/kg as iron.

EXAMPLE 4

A mixture of 187 ml of a 1 M aqueous solution of ferric chloride and 113 ml of a 1M aqueous solution of ferrous chloride was rapidly added with stirring to 827 ml of 1N sodium hydroxide at about 80° C. The solution was treated thereafter in the same way as in Example 1. 485 ml of the resulting aqueous sol of magnetic iron oxide (having a pH of 3.5 and an iron concentration of 25.8 mg/ml) was added to 340 ml of the aqueous solution of dextran prepared in Example 1. The mixture was heated under reflux for 40 minutes. The product was treated in the same way as in Example 1 to yield 22 g of a powdery complex. The product had an iron content of 44.1 W/W %, a saturation magnetic flux density of 32 emu/g, and an acute toxicity ($LD_{50}$) of 4400 mg/kg as iron.

EXAMPLE 5

Figure 3:
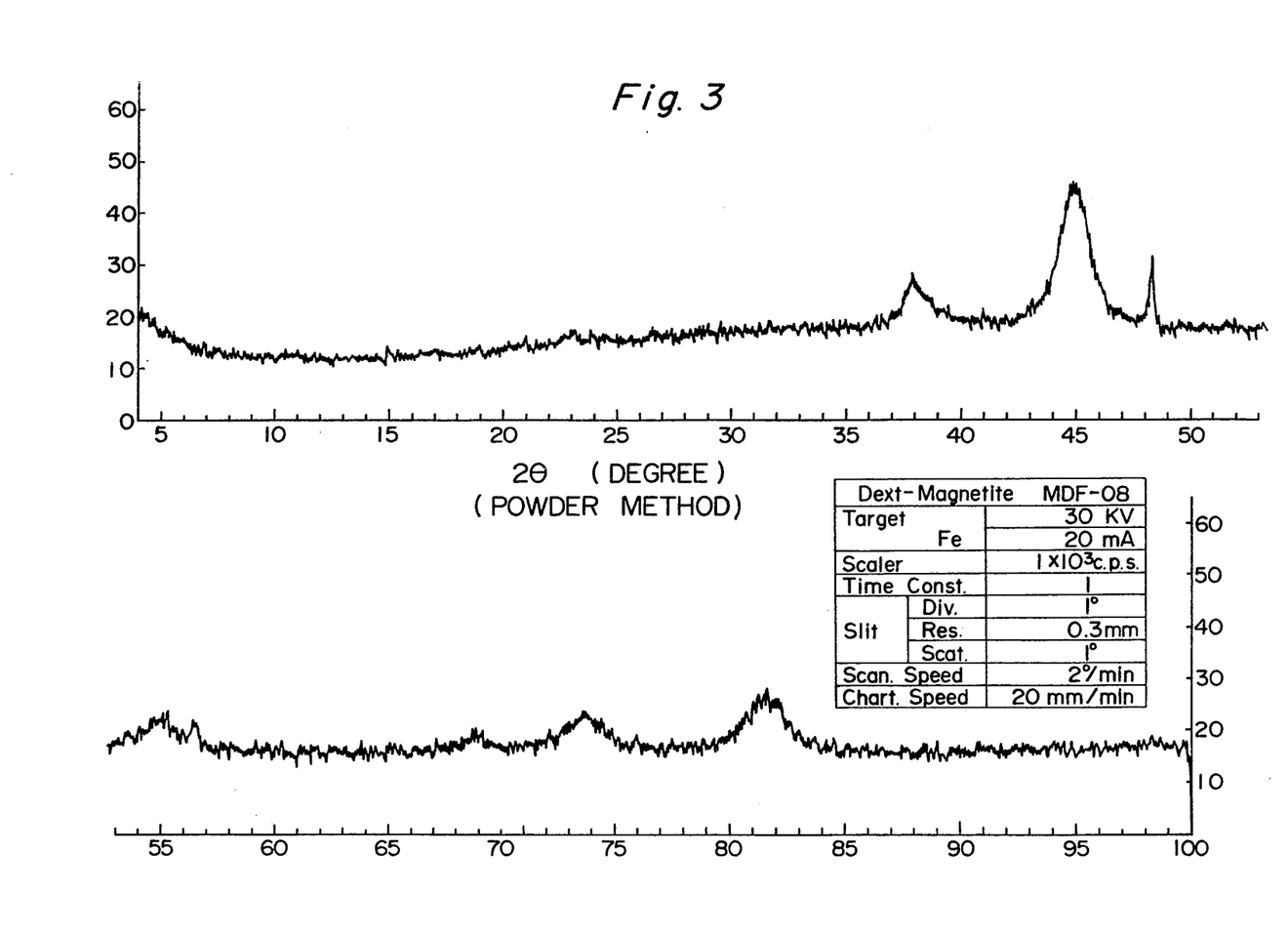
FIG. 3 is an X-ray diffraction chart of the complex obtained in Example 5 of the application.
Figure 4:
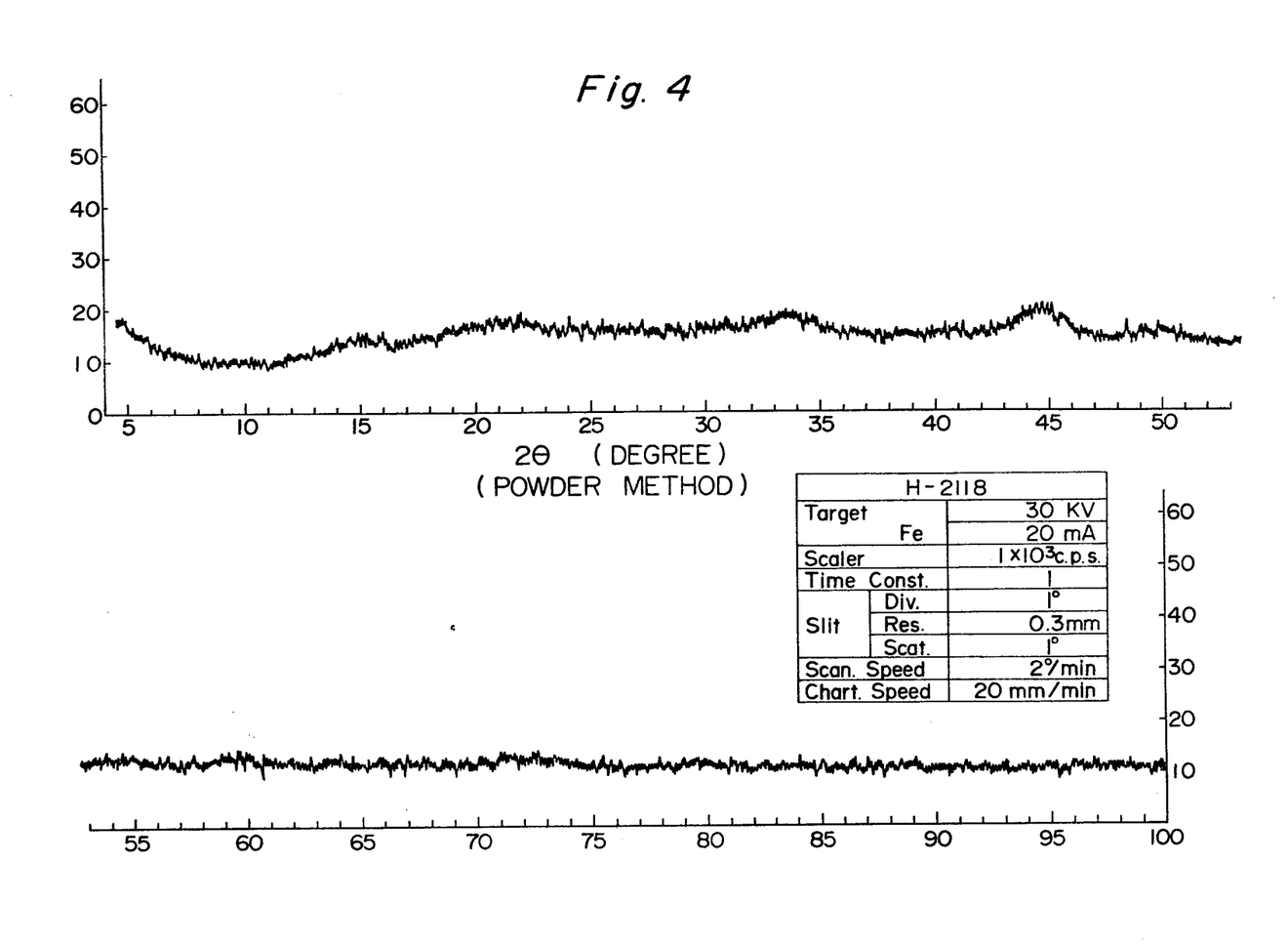
FIG. 4 is an X-ray diffraction chart of a conventional non-magnetic iron oxide-dextran complex obtained by using the same dextran as used in Example 1.
Figure 7:
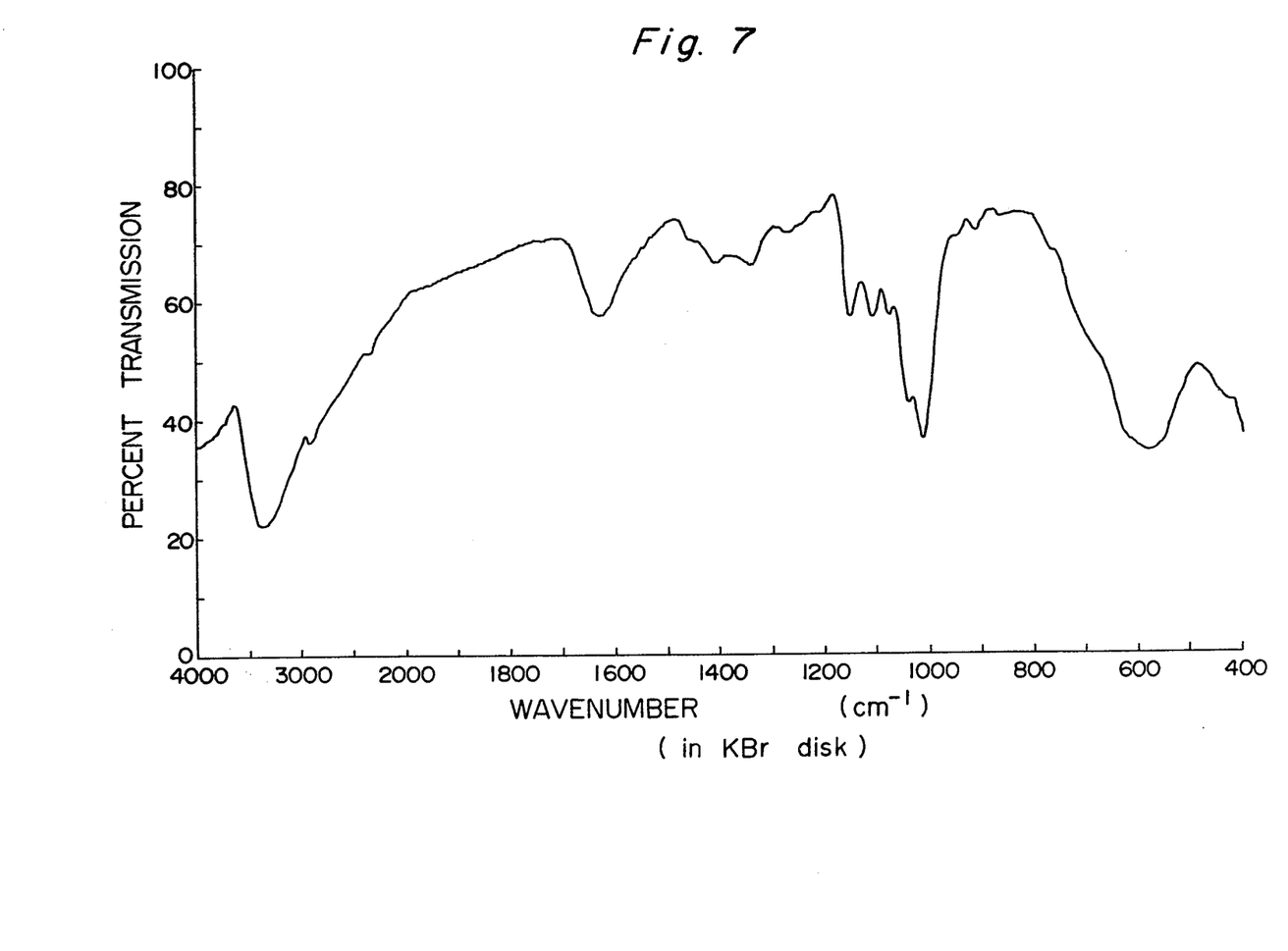
FIG. 7 is an infrared absorption spectrum chart of the complex of this invention obtained in Example 5.
Figure 8:
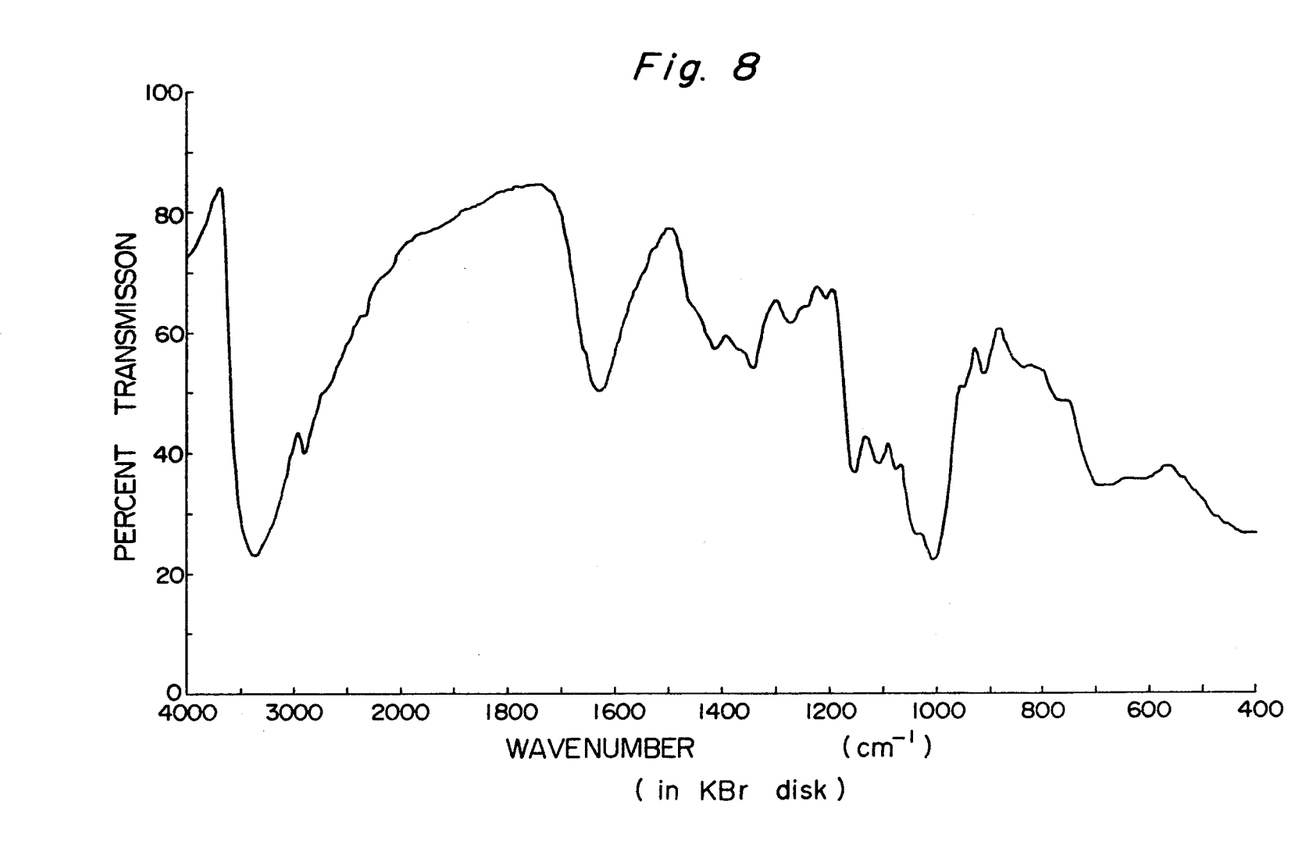
FIG. 8 is an infrared absorption spectrum chart of a conventional non-magnetic iron oxide-dextran complex obtained by using the same dextran as used in Example 1.

580 ml of water was added to 1000 ml of Amberlite IRA-410 (an ion-exchange resin, a product of Rohm & Haas Co.). A mixture of 200 ml of a 1M aqueous solution of ferric chloride and 100 ml of a 1M aqueous solution of ferrous chloride was added with stirring to the resulting slurry at a temperature of not more than 30° C. while maintaining the mixture at a pH of 8.0 to 8.7. Then, conc. hydrochloric acid was added to adjust the pH of the mixture to 1.5, and at this pH, the mixture was stirred for 1 hour. Then, the sol separated by filtration from the ion-exchange resin was dialyzed against running water for 10 hours to form an aqueous sol of magnetic iron oxide having a pH of 3.5 and an iron concentration of 12.8 mg/ml. 980 ml of the sol was added to 455 ml of the aqueous solution of dextran prepared in Example 1, and the mixture was heated under reflux for 40 minutes. After cooling, 1180 ml of methanol was added to precipitate the resulting complex. The complex was treated in the same way as in Example 1 to yield 22 g of a powdery complex which had an iron content of 45.3 W/W %. The product had a saturation magnetic flux density of 45 emu/g and an acute toxicity ($LD_{50}$) of 5500 mg/kg as iron. The X-ray diffraction chart of the complex obtained is shown in FIG. 3, and its infrared absorption spectrum chart is shown in FIG. 7.

EXAMPLE 6

200 g of dextran having an intrinsic viscosity of 0.042 was dissolved in 1000 ml of water, and 50 ml of a 40% aqueous solution of sodium hydroxide was added. The mixture was heated under reflux for 1.5 hours, and cooled. Then, acetone was added, and the precipitated dextran was separated and dissolved in water. The aqueous solution of dextran was treated in the same way as in Example 1. To 435 ml of the resulting aqueous solution having a dextran concentration of 23% was added 980 ml of the aqueous sol of magnetic iron oxide prepared in Example 5, and the mixture was heated under reflux for 1 hour. After cooling, 1210 ml of methanol was added to precipitate the complex obtained. The precipitate was treated in the same was as in Example 1 to afford 18 g of a powdery complex having an iron content of 54.1 W/W %, a saturation magnetic flux density of 50 emu/g, and an acute toxicity ($LD_{50}$) of 2100 mg/ml as iron.

EXAMPLE 7

410 ml of the aqueous solution of dextran prepared in Example 1 whose pH had been adjusted to 10 with 10N sodium hydroxide was added to 380 ml of 2N sodium hydroxide at about 70° C, and then with stirring a mixture of 180 ml fo a 1M aqueous solution of ferric chloride and 90 ml of a 1M aqueous solution of ferrous chloride was quickly added. The pH of the aqueous solution was adjusted to about 6.5 with conc. hydrochloric acid, and the solution was refluxed for 60 minutes. The reaction mixture obtained was centrifuged, and then filtered. 860 ml of methanol was added to the filtrate to precipitate the resulting complex. The precipitate was dissolved in water, and dialyzed against running water for 24 hours. It was concentrated at reduced pressure, filtered, and lyophilized. The yield of the dried product was 15 g. It had an iron content of 30.3%, and a saturation magnetic flux density of 15 emu/g.

What we claim is:

1. A water dispersable magnetic iron oxide-dextran complex wherein the proportion of the dextran, calculated as its anhydrous glucose unit, is about 0.1 to about 1 mole per mole of iron oxide, calculated as an iron atom.

2. An aqueous sol of the complex of claim 1 which is stable to the addition of an equal amount of a 20% aqueous solution of sodium chloride.

3. The complex of claim 1 which has a saturation magnetic flux density of more than 0 but not more than amount 90 emu/g.

4. The complex of claim 3 having a saturation magnetic flux density of from about 5 to about 80 emu/g.

5. The complex of claim 1 which shows in its X-ray diffraction a pattern having a diffraction intensity corresponding to a spinel structure.

6. The complex of claim 1 in the form of a solid powder having a saturation magnetic flux density of from 15 emu to 50 emu/g and an iron content of 30 to 45.5 w/w%.

7. A process for producing a magnetic iron oxide-dextran complex, which comprises reacting an aqueous sol of magnetic iron oxide with dextran having an intrinsic viscosity of about 0.02 to about 0.5 at a temperature of from about 50° to 120° C in an aqueous medium.

8. The process of claim 7 wherein the molar ratio of the aqueous sol of magnetic iron oxide to the dextran is 1 : about 1–5 calculated as the ratio of the iron atom of the oxide to the anhydrous glucose unit of the dextran.

9. The process of claim 8 wherein the molar ratio of the aqueous sol of magnetic iron oxide to the dextran is 1: about 1.5 to 3.

10. The process of claim 7 wherein the dextran has an intrinsic viscosity of from about 0.04 to about 0.1.

11. The process of claim 7 wherein the reaction is carried out at a temperature of from about 70° to about 110° C and under reflux.

12. The process of claim 7 wherein the magnetic iron oxide sol has a pH of 2.5 to 4.5.

13. The process of claim 7 wherein prior to the reaction, the dextran is modified by heating in an aqueous medium in the presence of a base selected from the group consisting of sodium hydroxide, potassium hydroxide and calcium hydroxide.

14. The process of claim 7 wherein the dextran is glucan having mainly an α-1,6-linkage formed by reacting a leuconostoc mesenteroide with sucrose.

* * * * *